US00PP36667P2

(12) United States Plant Patent
Ranney et al.

(10) Patent No.: US PP36,667 P2
(45) Date of Patent: May 13, 2025

(54) ***DEUTZIA* PLANT NAMED 'NCDX3'**

(50) Latin Name: ***Deutzia* sp.**
Varietal Denomination: NCDX3

(71) Applicant: North Carolina State University, Raleigh, NC (US)

(72) Inventors: Thomas Green Ranney, Arden, NC (US); Irene Palmer, Arden, NC (US); Nathan Lynch, Arden, NC (US); Andra Windorf Nus, Arden, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 18/745,766

(22) Filed: Jun. 17, 2024

(51) Int. Cl.
*A01H 5/00* (2018.01)
*A01H 6/48* (2018.01)

(52) U.S. Cl.
USPC ..... Plt./226

(58) Field of Classification Search
USPC ..... Plt./226
See application file for complete search history.

(56) References Cited

PUBLICATIONS https://www.gardencrossings.com/product/deutzia-yuki-kabuki-shrub-deutzia/. Retrieved from the Internet on Oct. 1, 2024.*
https://www.greatgardenplants.com/products/yuki-kabuki. retrieved from the Internet on Oct. 1, 2024.*

* cited by examiner

*Primary Examiner* — Susan Mccormick Ewoldt
(74) *Attorney, Agent, or Firm* — Cassandra Bright

(57) ABSTRACT

A new and distinct cultivar of *Deutzia* plant named 'NCDX3' is described, characterized by abundant, dark pink flowers buds and deep pink striped flowers. Plants have low-growing, compact habits. The new variety is a *Deutzia*, typically used as an ornamental garden or landscape plant.

3 Drawing Sheets

Latin name of the genus and species: *Deutzia* sp.
Variety denomination: 'NCDX3'.

BACKGROUND OF THE INVENTION

The present invention comprises a new and distinct *Deutzia* cultivar hereinafter referred to by the cultivar name 'NCDX3'. This new *Deutzia* was developed through a breeding program at a research nursery, located in Mills River, North Carolina. In 2013, the female parent, *Deutzia* 'NCDX2', U.S. Plant Pat. No. 28,347, was hybridized with the pollen parent *Deutzia xrosea* 'Carminea' (unpatented) x *gracilis* 'Nikko' (H2010-311-001, unpatented) to create a population of new hybrids. 'NCDX3' was selected from the population, based upon its combination of desirable traits, at the same nursery in 2014.

The first asexual propagation of 'NCDX3' occurred in July 2016 by rooting stem cuttings at a research nursery in Mills River, North Carolina. 'NCDX3' roots readily from softwood cuttings treated with a basal dip of 3000-5000 ppm indole butyric acid (potassium salt) in water. 'NCDX3' was repeatedly reproduced by vegetative cuttings over a seven-year period and has been found to retain its distinctive characteristics through successive asexual propagations.

Date of first public exposure was on Jun. 27, 2023, in the United States. This was made directly by the inventor or one who obtained the claimed invention directly or indirectly from the inventor. This sale and all public disclosures made between Jun. 27, 2023, and the filing of this application fall within the exception allowed under 102(b)(1).

SUMMARY OF THE INVENTION

The cultivar 'NCDX3' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'NCDX3'. These characteristics in combination distinguish 'NCDX3' as a new and distinct *Deutzia* cultivar:

1. Low-growing, compact habit.
2. Abundant, dark pink flowers buds and deep pink striped flowers.

PARENT COMPARISONS

Plants of the new cultivar 'NCDX3' are similar to plants of the seed parent in most horticultural characteristics. However, plants of the new cultivar 'NCDX3' differ in the following:

1. Plants of the new variety have a larger mature size than plants of the seed parent.
2. Flower buds of the new variety are darker pink than flowers of the seed parent.
3. Petals of the new variety have darker pink stripes than petals of the seed parent.

Plants of the new cultivar 'NCDX3' could not be compared to plants of the pollen parent as there is no record of its traits.

COMMERCIAL COMPARISON

'NCDX3' can be compared to the commercial variety *Deutzia* 'Magicien', unpatented. Plants of the new variety are similar to 'Magicien' in most horticultural characteristics, however, 'NCDX3' differs in the following:

1. Petal undersides of the new variety are bi-color, exhibiting a bright red-purple stripe with a pinkish-white border. Petal undersides of this comparator are also bicolor; however, the primary color is not as intense/deeply pigmented and the contrast between colors is not as evident.
2. Petal upper sides of the new variety are pure pinkish-white, while the petal upper sides of this comparator are pinkish-white with a darker pinkish color at the tip.
3. Plants of the new variety are not as tall as plants of this comparator.

BRIEF DESCRIPTION OF THE PHOTOGRAPHS

The accompanying photographs were taken using conventional techniques and although colors may appear different from actual colors due to light reflectance it is as accurate as possible by conventional photographic techniques.

DETAILED BOTANICAL DESCRIPTION

Figure 1:
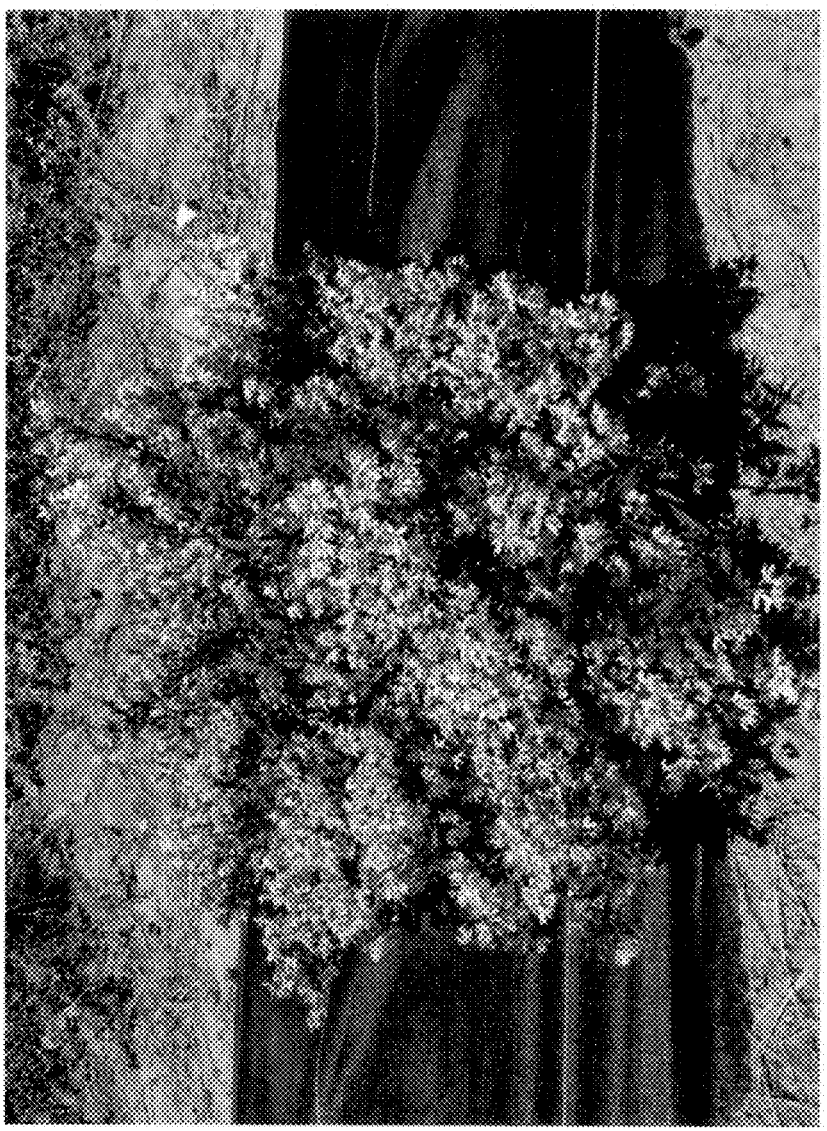
FIG. 1 is a photograph showing the habit of a three-year-old field-grown plant of 'NCDX3' in Spring of 2017, in Mills River, NC.
Figure 2:
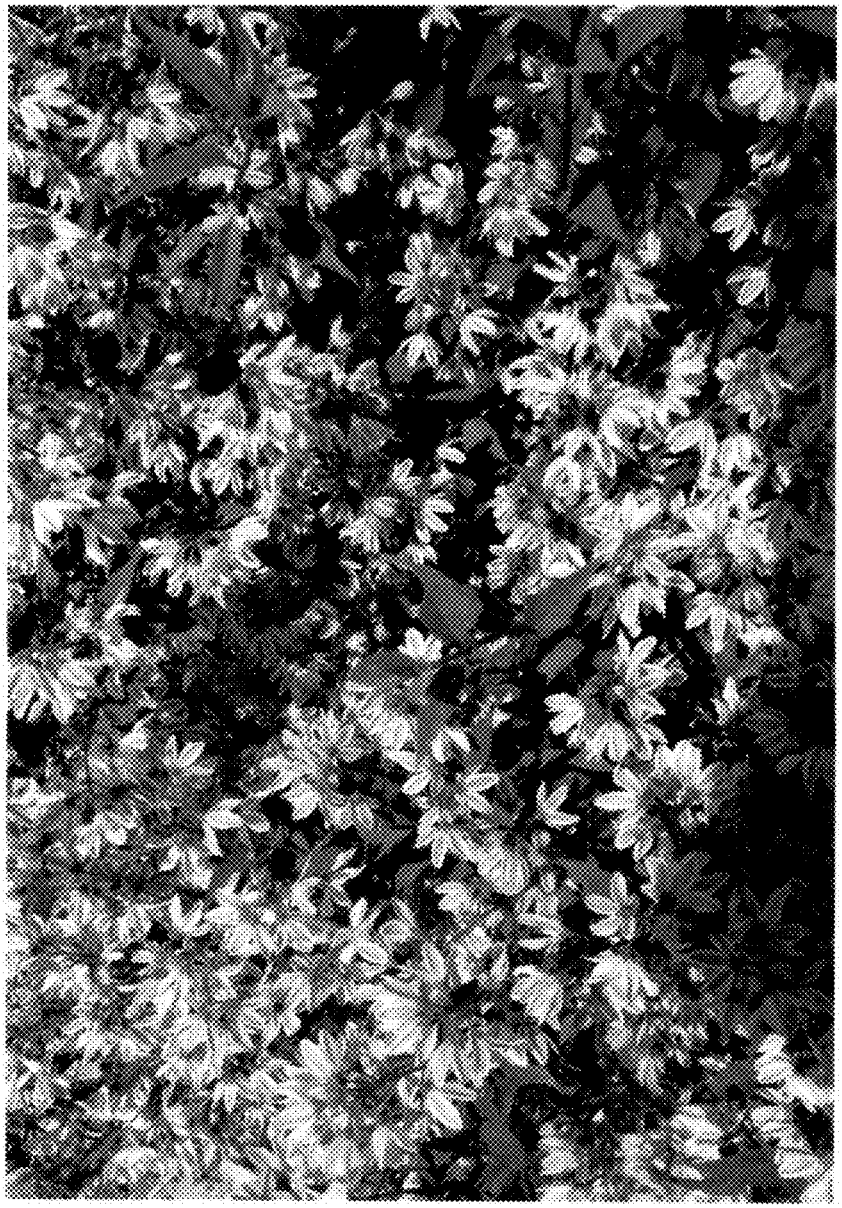
FIG. 2 is a photograph of the inflorescences of a five-year-old field-grown plant of 'NCDX3' in spring of 2019, in Mills River, NC.
Figure 3:
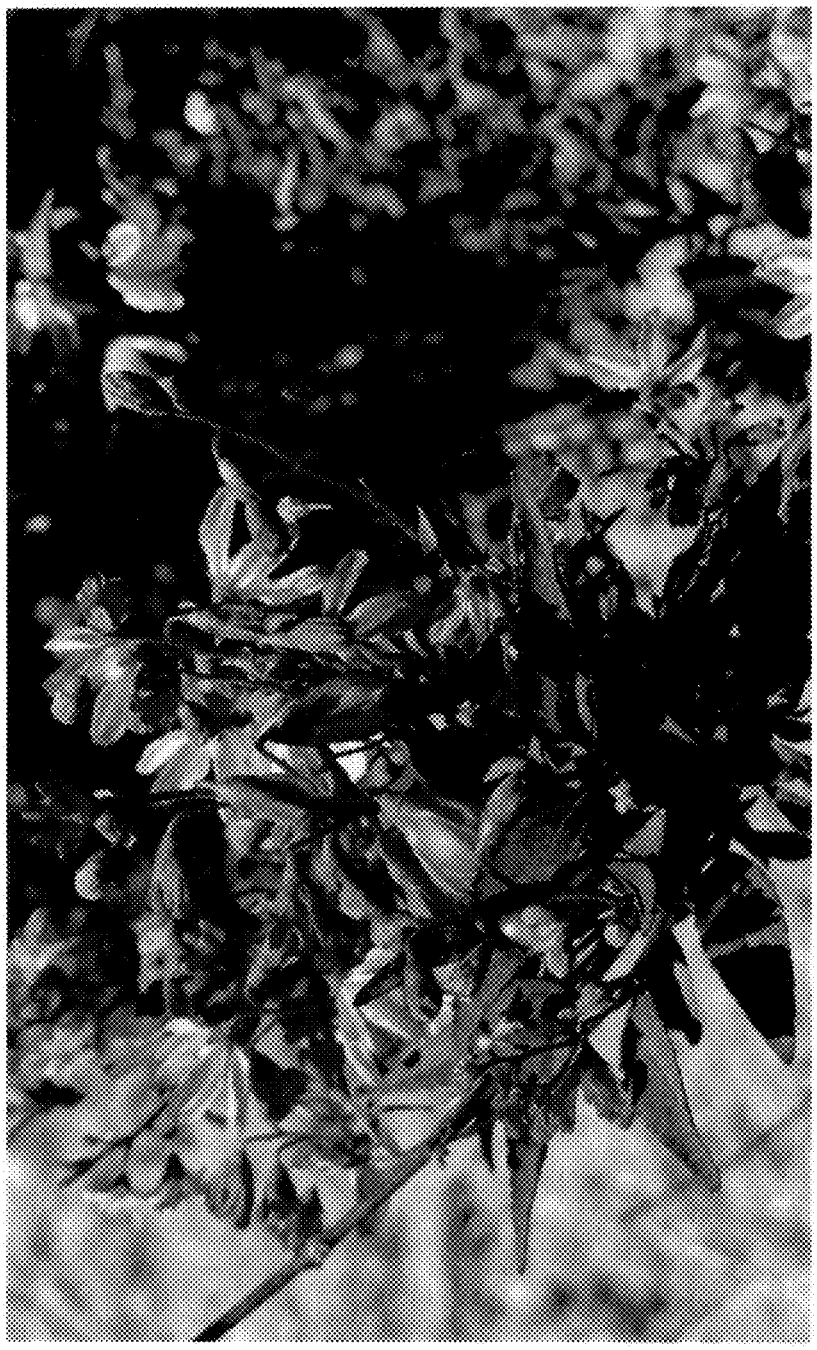
FIG. 3 is a photograph of the deep pink flower buds of a seven-year-old field-grown plant of 'NCDX3' in spring of 2023, in Mills River, NC.

The following is a detailed description of the botanical characteristics of the new and distinct *Deutzia* 'NCDX3'. The detailed description was taken from a three-year-old, container-grown plant, and also from a seven-year-old field-grown plant in Mills River, North Carolina in 2023. All colors cited herein refer to The Royal Horticultural Society Colour Chart (R.H.S.), London, Sixth Edition. Where specific dimensions, sizes, colors, and other characteristics are given, it is to be understood that such characteristics are approximations or averages set forth as accurately as practicable.

Botanical classification: *Deutzia* sp. 'NCDX3'.

PROPAGATION

Method: Softwood cuttings.

Time to initiate roots: 12 days at 18° to 27° C. in summer; 35 days in winter.

Time to produce rooted young plant: 20 days in summer; 60 days in winter.

Root description: Moderately dense, moderately branched, medium thickness, and fibrous. Off-white to beige in color, not accurately measured using R.H.S. chart.

PLANT

Age of plant described: 3 to 7 years old.

Growth habit: Low-growing, compact.

Height: 90 cm.

Plant spread: 120 cm.

Branches (woody branches 2-4 years old):

*Length*.—About 60 cm.

*Diameter*.—About 0.4 cm.

*Color*.—RHS Greyed-Green 197A.

*Texture*.—Glabrous with longitudinal fissures.

Shoots (current year's growth):

*Length*.—About 30 cm.

*Diameter*.—About 0.1 cm.

*Color*.—RHS Red-Brown 177A.

*Texture*.—Sparse, stellate pubescence.

Shoots (prior year's growth):

*Length*.—About 30 cm.

*Diameter*.—About 0.3 cm.

*Color*.—RHS Red-Brown 177A.

*Texture*.—Sparse, stellate pubescence.

Internode length: Average 1.3 cm.

FOLIAGE

Leaf:

*Arrangement*.—Opposite, single.

*Persistence*.—Deciduous.

*Length*.—Average 4.1 cm.

*Width*.—Average 1.4 cm.

*Shape*.—Lanceolate.

*Apex*.—Acuminate.

*Base*.—Attenuate.

*Margin*.—Slightly serrate.

*Texture, mature foliage*.—Top surface: Scabrous. Bottom surface: Glabrous.

*Color*.—Young foliage upper side: RHS Green 137A. Young foliage under side: RHS Yellow-Green 146B with some marginal coloration of Red 187B. Mature foliage upper side: RHS Green 137A. Mature foliage under side: RHS Yellow-Green 146A. Fall foliage: RHS Red 187A.

*Venation*.—Type: Pinnate. Color: Young foliage upper side: RHS Green 137A. Young foliage under side: RHS Red 187B. Mature foliage upper side: RHS Yellow-Green 146C. Mature foliage under side: RHS Yellow-Green 146C.

Petiole:

*Length*.—About 0.5 cm.

*Diameter*.—About 0.1 cm.

*Texture*.—Both sides glabrous.

*Color*.—RHS Yellow-Green 146B.

FLOWER

Natural flowering season: Mid-April to early May in Mills River, NC.

Flower type and habit: Single, star-shaped flowers on a terminal panicle.

Quantity of flowers: 5 to 9 per inflorescence.

Fragrance: None.

Inflorescence:

*Height*.—Average 5.9 cm.

*Diameter*.—Average 3.9 cm.

Bud:

*Shape*.—Ovoid.

*Length*.—About 0.7 cm.

*Diameter*.—About 0.5 cm.

*Color*.—RHS Purple-Red 71A.

*Texture*.—Glabrous.

Flower:

*Shape*.—Star-shaped.

*Diameter*.—Average 1.7 cm.

*Height*.—Average 1.2 cm.

Petals:
*Quantity.*—5 to 6.
*Arrangement.*—Whorl.
*Length.*—Average 1.3 cm.
*Width.*—Average 0.6 cm.
*Shape.*—Elliptic.
*Apex.*—Obtuse.
*Base.*—Attenuate.
*Margin.*—Entire.
*Texture, upper and lower surfaces.*—Glabrous.
*Color.*—When opening, inner side: RHS White N155C. When opening, outer side: Irregular stripes of RHS Purple-Red 64A on a background of White N155B. Fully opened, inner side: RHS White N155B. Fully opened, outer side: Irregular stripes of RHS Purple-Red 64A on a background of White N155B.

Sepals:
*Quantity.*—5 to 6.
*Arrangement.*—Whorl.
*Length.*—About 0.2 cm.
*Width.*—About 0.1 cm.
*Shape.*—Triangular.
*Apex.*—Acute.
*Base.*—Fused.
*Margin.*—Entire.
*Texture, upper and lower surfaces.*—Pubescent.
*Color.*—RHS Yellow-Green 146D.

Peduncles:
*Length.*—Average 4.9 cm.
*Diameter.*—About 0.1 cm.
*Texture.*—Sparsely pubescent.
*Color.*—RHS Yellow-Green 146C.

Pedicels:
*Length.*—Average 4.9 cm.
*Diameter.*—Less than 0.1 cm.
*Color.*—RHS Yellow-Green RHS 146C.
*Texture.*—Pubescent.

REPRODUCTIVE ORGANS

Gynoecium:
*Pistil number.*—4.
*Pistil length.*—About 0.5 cm.
*Style length.*—About 0.4 cm.
*Style color.*—RHS White 155D.
*Stigma shape.*—Irregularly globoid.
*Stigma color.*—RHS White 155D.
*Ovary shape.*—Oval.
*Ovary color.*—RHS Yellow-Green 146B.

Androecium:
*Stamen number.*—9.
*Anther shape.*—Round.
*Anther length.*—Less than 0.1 cm.
*Pollen color.*—RHS Yellow 12B.

OTHER CHARACTERISTICS

Fruit and seed: None observed.

Disease/pest resistance: Neither resistance nor susceptibility to the normal pests and diseases of *Deutzia* has been observed.

Cold hardiness: At least USDA zone 6b; testing has not been completed in colder zones.

What is claimed is:

1. A new and distinct cultivar of *Deutzia* plant named 'NCDX3', substantially as illustrated and described herein.

* * * * *